United States Patent

Wroblowsky et al.

[11] Patent Number: 5,606,074
[45] Date of Patent: Feb. 25, 1997

[54] PROCESS FOR THE PREPARATION OF PYRAZOLES

[75] Inventors: Heinz-Jürgen Wroblowsky, Langenfeld; Reinhard Lantzsch, Wuppertal, both of Germany

[73] Assignee: Bayer Aktiengesellschaft, Leverkusen, Germany

[21] Appl. No.: 610,773

[22] Filed: Mar. 4, 1996

[30] Foreign Application Priority Data

Mar. 7, 1995 [DE] Germany .................. 195 07 915.9

[51] Int. Cl.⁶ .................. C07D 207/323; C07D 207/325
[52] U.S. Cl. .................. 548/373.1; 548/375.1; 548/376.1; 548/377.1
[58] Field of Search .................. 548/373.1, 376.1, 548/377.1, 375.1

[56] References Cited

U.S. PATENT DOCUMENTS 5,118,853   6/1992   Lee et al. .................. 564/502

FOREIGN PATENT DOCUMENTS

0526281A1   2/1993   European Pat. Off. .
1234223     2/1967   Germany .
1670692     6/1971   Germany .
2310185     9/1974   Germany .

OTHER PUBLICATIONS

H. Bredereck et al., Chemische Berichte, vol. 93, No. 5, pp. 1208–1211 (1960).
CA93: 45871 Orthoamides. XXXIV. Syntheses with vinylidenediamines. Kantlehner et al. p. 856. 1980.

CA117: 191344 Preparation of ... intermediates. Lee et al., p. 749. 1992.

Primary Examiner—Joseph McKane
Attorney, Agent, or Firm—Sprung Horn Kramer & Woods

[57] ABSTRACT

The invention relates to a process for the preparation of pyrazoles of the formula (I)

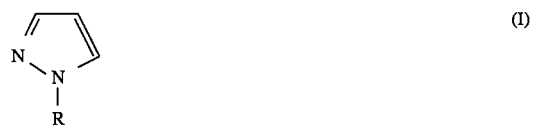

in which
R represents hydrogen, alkyl, unsubstituted or substituted cycloalkyl, unsubstituted or substituted aryl or unsubstitited or substituted arylalkyl,
by reaction of propenylideneammonium chloride derivatives of the formula (II)

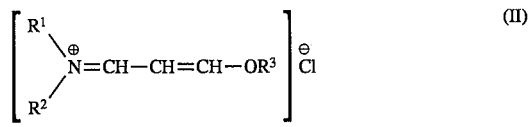

with hydrazines of the formula (III)

$$H_2N-NH-R \qquad (III).$$

1 Claim, No Drawings

PROCESS FOR THE PREPARATION OF PYRAZOLES

The invention relates to a novel process for the preparation of pyrazoles.

It is known that pyrazoles are obtained if hydrazines of the formula (A) are reacted with 3-dimethylaminoacrolein of the formula (B) in accordance with the following reaction diagram:

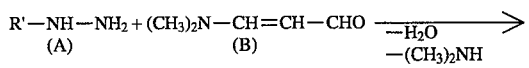

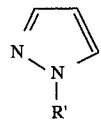

(cf. in this context German Offenlegungsschrit 1 670 692 or Coll. czechoslov. chem. Commun. 23, 452 (1958)).

However, this process has the disadvantage that the starting materials of the formula (B) are only available in unsatisfactory yields, in particular with regard to an industrial process (cf. e.g. the abovementioned literature reference and Zh. Org. Khim 8, 1394 (1972) and U.S. Pat. No. 5,118,853) and their necessary isolation by distillation entails a considerable additional expenditure.

It is further known that pyrazoles can be obtained if, e.g., dimethylformamide is admixed with phosgene, the resulting formylation agent of the formula (C) is reacted with an enamine of the formula (D) and finally the salt-like intermediate of the formula (E) thus obtained is reacted with hydrazines of the formula (A) in accordance with the following reaction diagram:

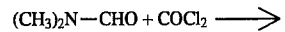

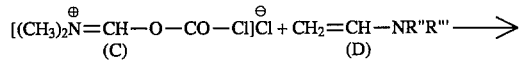

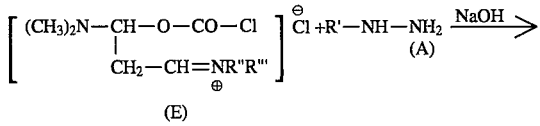

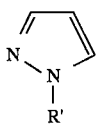

(cf. in this context German Offenlegungsschrift 1 234 223).

However, this process has the disadvantage that some of the enamines of the formula (D) are not readily accessible or possess a toxic potential. In addition, recycling or disposing of the amine liberated on ring closure entails a relatively high expenditure.

It has now been found that pyrazoles of the formula (I)

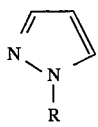

in which

R represents hydrogen, alkyl, unsubstituted or substituted cycloalkyl, unsubstituted or substituted aryl or unsubstitited or substituted arylalkyl, are obtained, if propenylideneammonium chloride derivatives of the formula (II)

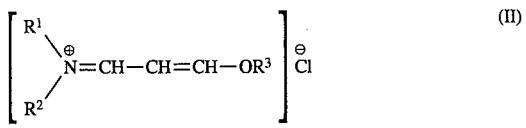

in which

R$^1$ and R$^2$ are identical or different and represent alkyl and

R$^3$ represents alkyl, are reacted with hydrazines of the formula (III)

in which

R has the meaning given above, in the presence of a base and in the presence of a diluent.

Surprisingly, by means of the process according to the invention, pyrazoles of the formula (I) can be obtained in very good yields and in high purity, although according to the prior art it had to be expected that this reaction would only proceed successfully if; prior to the reaction, the propenylideneammonium chlorides of the formula (II) are hydrolyzed to the corresponding free bases of the formula (IIa)

in which

R$^1$ and R$^2$ have the meaning given above.

The reaction of the invention thus has the advantage of a more favourable process procedure with simultaneous improvement in yield, in particular with respect to the overall process, i.e. including the precursor preparation.

The process of the invention is preferably used for the preparation of pyrazoles of the formula (I) in which R represents hydrogen, straight-chain or branched $C_1$-$C_4$-alkyl or $C_3$-$C_6$-cycloalkyl which is optionally monosubstituted to trisubstituted with identical or different substituents, the substituents used being halogen, $C_1$-$C_4$-alkyl, $C_1$-$C_4$-alkoxy, $C_1$-$C_4$-halogenoalkyl and $C_1$-$C_4$-halogenoalkyloxy, each of which is straight-chain or branched, or phenyl or benzyl, each of which is optionally monosubstituted to trisubstituted with identical or different substituents, in each case the substituents used being halogen, cyano, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-4-halogenoalkoxy and $C_1$-$C_4$-halogenoalkylthio (having in each case 1 to 9 identical or different halogen atoms, in particular fluorine and chlorine atoms), each of which is optionally straight-chain or branched, and phenyl which is optionally monosubstituted or disubstituted by halogen and/or straight-chain or branched $C_1$-$C_4$-alkyl.

The process of the invention is particularly preferably used for the preparation of pyrazoles of the formula (I) in which R represents hydrogen, methyl, ethyl, n- or i-propyl, n-, i-, s- or t-butyl or cyclopentyl or cyclohexyl, each of which is optionally monosubstituted or disubstituted with identical or different substituents, the substituents used being fluorine, chlorine, bromine, methyl, ethyl, trifluoromethyl and trifluoromethoxy, or phenyl or benzyl, each of which is optionally monosubstituted to trisubstituted with identical or different substituents, in each case the substituents used being fluorine, chlorine, cyano, nitro, methyl, ethyl, n- or i-propyl, n-, i-, s- or t-butyl, trifluoromethyl, trifluoromethoxy, trifluoromethylthio and phenyl which is optionally monosubstituted or disubstituted by fluorine, chlorine and/or methyl.

If, for example, 3-ethoxypropenylidenedimethylammonium chloride and hydrazine hydrate are used as starting materials, the course of the reaction of the process of the invention can be outlined by the following formula diagram:

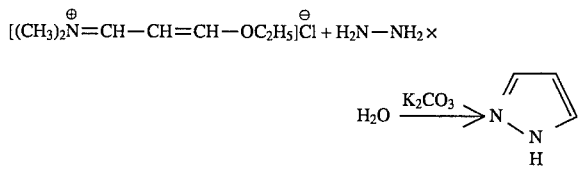

The propenylideneammonium chloride derivatives to be used as starting materials in the process of the invention are defined in general by the formula (II). In the formula (II), $R^1$ and $R^2$ are identical or different and preferably represent straight-chain or branched $C_1$-$C_4$-alkyl, in particular methyl, ethyl, n- or i-propyl, n- or i-butyl. $R^3$ preferably represents straight-chain or branched $C_1$-$C_4$-alkyl, in particular methyl, ethyl, n- or i-propyl, n- or i-butyl.

The propenylideneammonium chloride derivatives of the formula (II) are known in principle (cf. e.g. U.S. Pat. No. 5,118,953).

They are obtained by reacting dialkylformamides of the formula (IV)

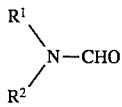

in which $R^1$ and $R^2$ have the meaning given above, with acid chlorides, such as oxalyl chloride, phosgene, phosphorus oxychloride or thionyl chloride in the presence of a diluent such as methylene chloride at temperatures between 0° C. and 50° C. and directly reacting the resulting intermediates of the formula (V)

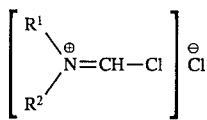

in which $R^1$ and $R^2$ have the meaning given above, without isolation, with vinyl ethers of the general formula (VI)

in which $R^3$ has the meaining given above.

The propenylideneammonium chloride derivatives of the formula (II) are preferably produced with 0.5 to 1.0 equivalents of additionally bound hydrogen chloride (cf. also the preparation examples).

The dimethylformamides of the formula (IV) and the vinyl ethers of the formula (VI) are generally known compounds of organic chemistry.

The hydrazines also to be used as starting materials in the process of the invention are generally defined by the formula (III). In the formula (III), R preferably, or particularly preferably, has the meaning which has already been given above as preferred or particularly preferred for R in connection with the description of the pyrazoles of the formula (I) to be prepared according to the invention.

The hydrazines of the formula (III) are generally known compounds of organic chemistry. The unsubstituted hydrazine (R=H) is preferably used in the hydrate form.

The process of the invention is carried out in the presence of a base. All conventional inorganic or organic bases can be used for this. Those which can be preferably used are alkali metal hydroxides and alkaline earth metal hydroxides, alkali metal amides and alkaline earth metal amides, alkali metal alkoxides and alkaline earth metal alkoxides, alkali metal carbonates and alkaline earth metal carbonates and alkali metal hydrogen carbonates and alkaline earth metal hydrogen carbonates, such as sodium hydroxide, potassium hydroxide, sodium amide, sodium methoxide, sodium ethoxide, potassium tertbutoxide, sodium carbonate, potassium carbonate, calcium carbonate, potassium hydrogen carbonate and sodium hydrogen carbonate; in addition, trialkylamines, such as trimethylamine, triethylamine and tributylamine; and dialkylamines, such as dibutylamine or, in particular, the dialkylamines corresponding to the dialkylformamide of the formula (IV) used.

The process of the invention is carried out in the presence of a diluent.

Diluents which are suitable are conventional organic solvents such as water. These preferably include alcohols, such as ethanol; ethers, such as diethyl ether, diisopropyl ether, methyl tert-butyl ether and tetrahydrofuran; and optionally halogenated hydrocarbons, such as dichloromethane, chloroform and tetrachloromethane.

The reaction temperatures can be varied in a relatively wide range when the process of the invention is carried out. Generally, temperatures between 0° C. and 150° C., preferably temperatures between 20° C. and 80° C., are employed.

To carry out the process of the invention, per mole of propenylideneammonium chloride derivative of the formula (II), generally 1 to 3 mol, preferably 1 to 1.5 mol, of hydrazine of the formula (III) are used and 1 to 3 mol, preferably 1 to 1.5 mol, of base.

The reaction components can be used in any order when the process of the invention is carried out.

In a particular embodiment of the process of the invention, it is also possible further to react the starting products of the formula (II) directly without isolation after their preparation (cf. also the preparation examples).

The products can be worked up in a conventional manner (cf. also the preparation examples).

The pyrazoles of the formula (I) to be prepared by the process of the invention can be used as intermediates for the preparation of biologically active compounds, for example insecticides (cf., e.g., EP-A-438 690).

PREPARATION EXAMPLES:

Example 1

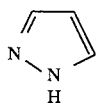

27.2 g (0.54 mol) of hydrazine hydrate are dissolved in 300 ml of ethanol and, after addition of 75.2 g (0.54 mol) of potassium carbonate, the solution of 104.5 g (0.54 mol) of 3-ethoxypropenylidenedimethylammonium chloride hydrochloride (Example II–1) in 50 ml of ethanol is added dropwise at 25° to 35° C. After addition is completed, the mixture is stirred overnight at room temperature. It is then filtered, washed with methyl tert-butyl ether, and the filtrate is concentrated by evaporation. To remove the salts, the residue is stirred with methyl tert-butyl ether, the insoluble salts are filtered off and the filtrate is concentrated by evaporation.

The crude product thus obtained is distilled in vacuo at 0.5 mbar and a bath temperature of 100° to 120° C.

31.0 g (84.4% of theory) of pyrazole having a purity of 98.5% are obtained.

$^1$H-NMR (ppm in d$^6$-DMSO): 6.261 (tr, 1H); 7.610 (s, 2H); 12.843 (broad s, 1H).

(Without Isolation of the Starting Product of the Formula II)

36.5 g (0.5 mol) of dimethylformamide are introduced into 250 ml of dichloroethane and 22 g (0.22 mol) of phosgene are passed in at 0° C. 20 g (0.2 mol) of butyl vinyl ether are then added dropwise at 0° C., the mixture is allowed to come to room temperature and is then heated for 15 minutes at 70° C. The mixture is then allowed to cool, 80 g of ice are added and 70 ml of saturated potassium carbonate solution are added dropwise. At a bath temperature of 100° C., the dichloroethane is distilled off and 10 g (0.2 mol) of hydrazine hydrate are then added dropwise at 70° C. After addition is completed, the mixture is heated for 10 minutes at 95° C. and is then allowed to cool. After the reaction solution is worked up, 10.9 g (80.3% of theory) of pyrazole are obtained.

According to Example 1 and in accordance with the general process details, the following pyrazoles of the formula (I)

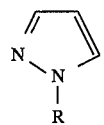

(I)

are obtained:

TABLE 1

| Example No. | R | $^1$H-NMR(d$^6$-DMSO) ppm |
|---|---|---|
| 2 | CH$_3$ | 3.831(s, 3H), 6.216(tr, 1H), 7.406(d, 1H), 7.661(d, 1H) |
| 3 | C(CH$_3$)$_3$ | 1.508(s, 9H), 6.210(tr, 1H), 7.430(d, 1H), 7.782(dd, 1H) |
| 4 | 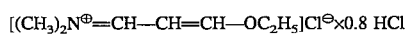 | 6.558(dd, 1H), 7.313(m, 1H), 7.481(m, 2H), 7.766(d, 1H), 7.853(m, 2H), 8.201(dd, 1H) |
| 5 | 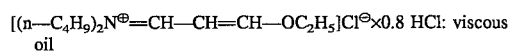 | 6.690(dd, 1H), 7.947(d, 1H), 8.050(dd, 1H), 8.304(dd, 1H), 8.390(tr, 1H) |

TABLE 1-continued

| Example No. | R | $^1$H-NMR(d$^6$-DMSO) ppm |
|---|---|---|
| 6 | 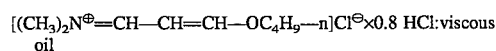 | 6.590(tr, 1H), 7.845(d, 1H), 8.086(d, 1H), 8.226(s, 1H) |

Preparation of the Starting Products of the Formula (II)

Example (II-1)

[(CH$_3$)$_2$N$^\oplus$=CH—CH=CH—OC$_2$H$_5$]Cl$^\ominus$×0.8 HCl

Under a protective gas, 109.5 g (1.5 mol) of dimethylformamide are admixed with 800 ml of methylene chloride and in the course of 3 hours 215 g (1.7 mol) of oxalyl chloride are added dropwise at 5° to 10° C. The mixture is allowed to come to room temperature and in the course of 45 minutes 121 g (1.68 mol) of ethyl vinyl ether are added to the white suspension (highly exothermic) at 25° to 28° C. The red-brown reaction mixture is then stirred for 30 minutes at 37° to 40° C. and the methylene chloride is subsequently distilled off at 30 mm Hg and 45° C. bath temperature.

285.6 g (95.2% of theory) of crude 3-ethoxypropenylidenedimethylammonium chloride hydrochloride are obtained, which are further reacted directly.

$^1$H-NMR (ppm in d$^6$-DMSO): 1.336 (tr, 3H); 3.391 (s, 3H); 3.529 (s, 3H); 4.360 (g, 2H); 6.380 (tr, 1H); 8.218 (d, 1H); 8.778 (d, 1H); 14.234 (s, 8H).

In accordance with Example (II-1) and in correspondence with the general process details, the following starting products of the formula (II) are obtained:

Example (II-2)

[(n—C$_4$H$_9$)$_2$N$^\oplus$=CH—CH=CH—OC$_2$H$_5$]Cl$^\ominus$×0.8 HCl: viscous oil Example (II-3)

[(CH$_3$)$_2$N$^\oplus$=CH—CH=CH—OC$_4$H$_9$—n]Cl$^\ominus$×0.8 HCl: viscous oil

We claim:
1. A process for the preparation of a pyrazole of the formula

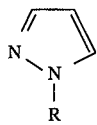

(I)

in which
R represents hydrogen, alkyl, unsubstituted or substituted cycloalkyl, unsubstituted or substituted aryl or unsubstituted or substituted arylalkyl,
which comprises reacting a propenylideneammonium chloride compound of the formula

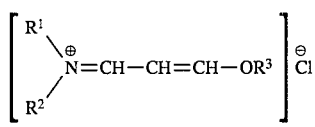
in which
R¹ and R² are identical or different and represent alkyl and R³ represents alkyl,
with a hydrazine of the formula
$$H_2N-NH-R \qquad (III)$$
in which
R has the meaning given above,
in the presence of a base and in the presence of a diluent.
* * * * *